US012734158B2

(12) United States Patent
Zhang et al.

(10) Patent No.: US 12,734,158 B2
(45) Date of Patent: Sep. 15, 2026

(54) APPLICATION OF RILUZOLE- AND BORNEOL-CONTAINING COMPOSITION IN PREPARATION OF MEDICATION FOR TREATING CEREBROVASCULAR DISEASES

(71) Applicant: NEURODAWN PHARMACEUTICAL CO., LTD., Nanjing (CN)

(72) Inventors: Zhengping Zhang, Nanjing (CN); Lei Wang, Jiangsu (CN); Rong Chen, Nanjing (CN)

(73) Assignee: NEURODAWN PHARMACEUTICAL CO., LTD., Nanjing (CN)

( * ) Notice: Subject to any disclaimer, the term of this patent is extended or adjusted under 35 U.S.C. 154(b) by 357 days.

(21) Appl. No.: 18/272,691

(22) PCT Filed: Jan. 26, 2022

(86) PCT No.: PCT/CN2022/073909

§ 371 (c)(1),
(2) Date: Jul. 17, 2023

(87) PCT Pub. No.: WO2022/166695

PCT Pub. Date: Aug. 11, 2022

(65) Prior Publication Data

US 2024/0165087 A1 May 23, 2024

(30) Foreign Application Priority Data

Feb. 2, 2021 (CN) ......................... 202110141522.3

(51) Int. Cl.

*A61K 31/428* (2006.01)
*A61K 31/045* (2006.01)
*A61P 9/10* (2006.01)

(52) U.S. Cl.

CPC .......... *A61K 31/428* (2013.01); *A61K 31/045* (2013.01); *A61P 9/10* (2018.01)

(58) Field of Classification Search

CPC .................................................... A61K 31/428
See application file for complete search history.

(56) References Cited

U.S. PATENT DOCUMENTS

2018/0318261 A1 11/2018 Yang et al.

FOREIGN PATENT DOCUMENTS

| | | | |
|---|---|---|---|
| CN | 102485223 | A | 6/2012 |
| CN | 103070861 | A | 5/2013 |
| CN | 104224772 | A | 12/2014 |
| CN | 107613976 | A | 1/2018 |
| WO | WO 2016/197945 | A1 | 12/2016 |

OTHER PUBLICATIONS

Chen, Z-x. et al., "Borneol for Regulating the Permeability of the Blood-Brain Barrier in Experimental Ischemic Stroke: Preclinical Evidence and Possible Mechanism," *Oxidative Medicine and Cellular Longevity*, art. ID 2936737 (2019): 1-15.

Extended European Search Report issued in European Patent Application No. 22748974.7, dated Sep. 27, 2024.

Verna, S. K. et al., "Enhancement in the Neuroprotective Power of Riluzole Against Cerebral Ischemia Using a Brain Targeted Drug Delivery Vehicle," ACS Appl. Mater. Interfaces, 8 (2016): 19716-19723.

Borneolum, *Chinese Pharmacopoeia*, 2020: 61.

Doble, A., "The pharmacology and mechanism of action of riluzole," *Neurology*, 17 (1996): 233S-241S.

Dong, T. et al., "The protective roles of L-borneolum, D-borneolum and synthetic borneol in cerebral ischaemia via modulation of the neurovascular unit," *Biomedicine & Pharmacotherapy*, 102 (2018): 874-883.

Jiajia, C. et al., "Neuroprotective effect of borneol and its analogues on glutamic acid induced neuron injury," *ACTA Universitatis Medicinalis Nanjing* (*Natural Science*), 33 (2013): 630-635.

Jing, L. et al., "Research Advances in Mechanism of Blood-Brain Barrier Opening by Borneol and Clinical Uses thereof," *Journal of Chengdu Medical College*, 8 (2013): 628-631.

Granger, R. E. et al., "(+)- and (−)-borneol: efficacious positive modulators of GABA action at human recombinant $\alpha_1\beta_{2\gamma 2L}$ $GABA_A$ receptors," *Biochemical Pharmacology*, 69 (2005): 1101-1111.

Li, H-l. et al., "Research Progress on Pharmacological Action of Riluzole," *Key Laboratory for Space Bioscience and Biotechnology, School of Life, Northwestern Polytechnical University*, 14 (2015): 1165-1168.

Liu, L. et al., "Research Progress of Riluzole on Neuroprotection, Analgesia and Anti-Depressant Applications," *Key Laboratory for Space Bioscience and Biotechnology, School of Life, Northwestern Polytechnical University*, 34 (2017): 6-9.

Liu, J. et al., "The efficacy and safety of riluzole for neurodegenerative movement disorders: a systematic review with meta-analysis," *Drug Delivery*, 25 (2018): 43-48.

PCT International Search Report and Written Opinion issued in International Patent Application No. PCT/CN2022/073909, mailed Apr. 27, 2022.

Pratt, J. et al., "Neuroprotective actions of riluzole in rodent models of global and focal cerebral ischaemia," *Neuroscience Letters*, 140 (1992): 225-230.

Stutzmann, J. M. et al., "Neuroprotective Profile of Riluzole in In Vivo Models of Acute Neurodegenerative Diseases," *CNS Drug Reviews*, 3 (1997): 83-101.

Tao, W. et al., "Neuroprotective effect of riluzole against early brain injury after subarachnoid hemorrhage in rats," *Chinese J Minim Invasive Neurosurg*, 24 (2019): 416-420.

Wahl, F. et al., "Effect of riluzole on focal cerebral ischemia in rats," *European Journal of Pharmacology*, 230 (1993): 209-214.

(Continued)

*Primary Examiner* — Yong S. Chong
(74) *Attorney, Agent, or Firm* — pH IP Law

(57) ABSTRACT

A composition applied to preparation of a medicament for treating cerebrovascular diseases, in particular ischemic cerebrovascular diseases. The composition contains 2-amino-6-trifluoromethoxybenzothiazole or a pharmaceutically acceptable salt thereof and borneol. By means of the compatibility between 2-amino-6-trifluoromethoxybenzothiazole and d-borneol, according to non-clinical cell test and animal efficacy test results, for cerebrovascular diseases, 2-amino-6-trifluoromethoxybenzothiazole and d-borneol have the effect of synergistically increasing efficacy.

8 Claims, 10 Drawing Sheets

(56) References Cited

OTHER PUBLICATIONS

Zhang, Q-L. et al., "Borneol, a novel agent that improves central nervous system drug delivery by enhancing blood-brain barrier permeability," *Drug Delivery*, 24 (2017): 1037-1044.

Zhang, Z. et al., "Compound edaravone alleviates lipopolysaccharide (LPS)-induced acute lung injury in mice," *European Journal of Pharmacology*, 811 (2017): 1-11.

Zheng, Q. et al., "Borneol, a messenger agent, improves central nervous system drug delivery through enhancing blood-brain barrier permeability: a preclinical systematic review and meta-analysis," *Drug Delivery*, 25 (2018): 1617-1633.

Zhongjian, C. et al., "Research Advances in Effects of Borneol on Enhancing Drug Transport across the Blood Brain Barrier," *Chinese Traditional Patent Medicine*, 41 (2019): 2170-2173.

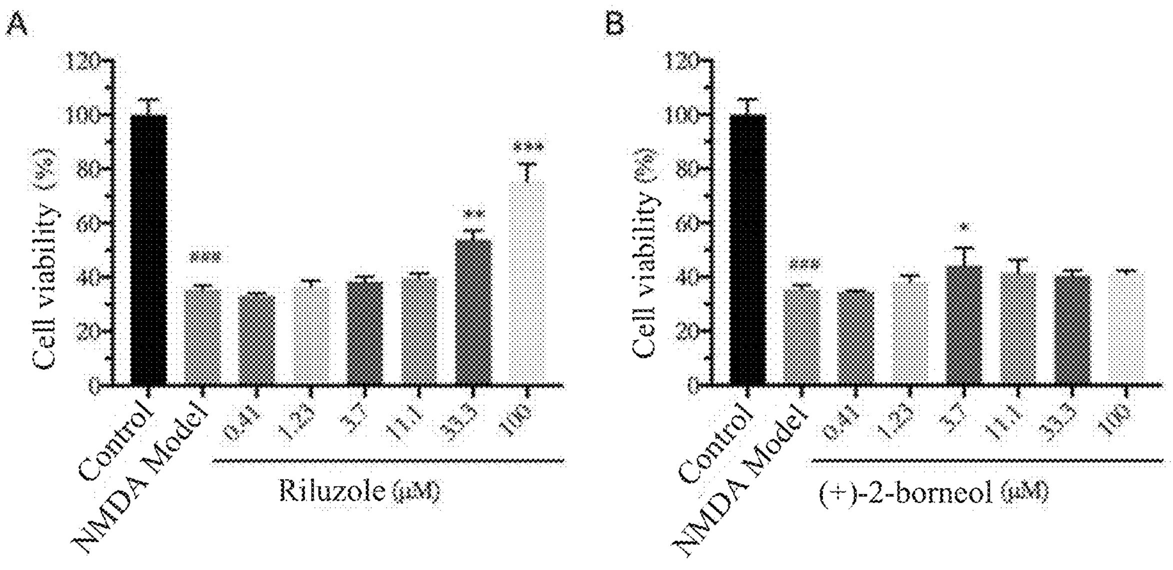
FIG. 1A-B
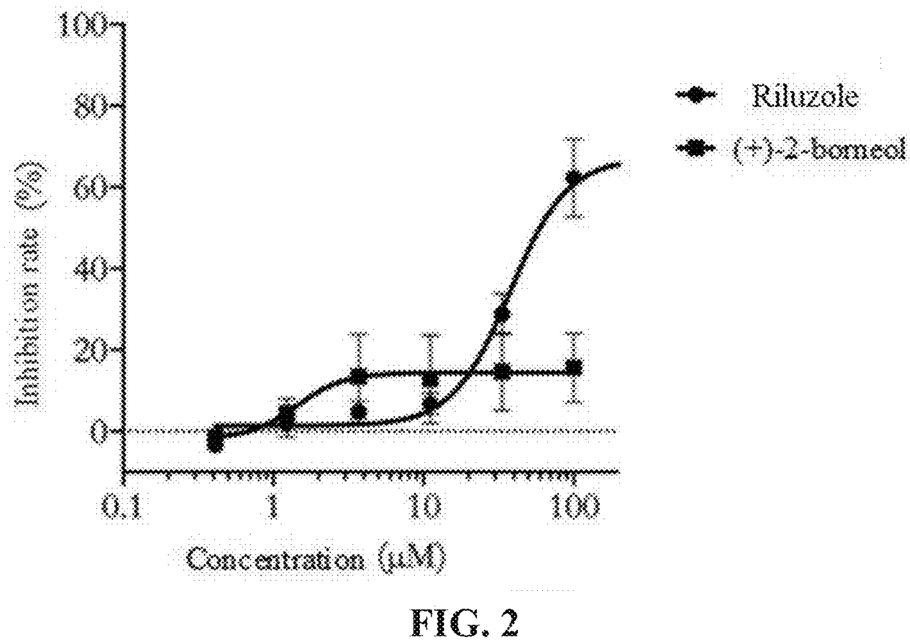
FIG. 2

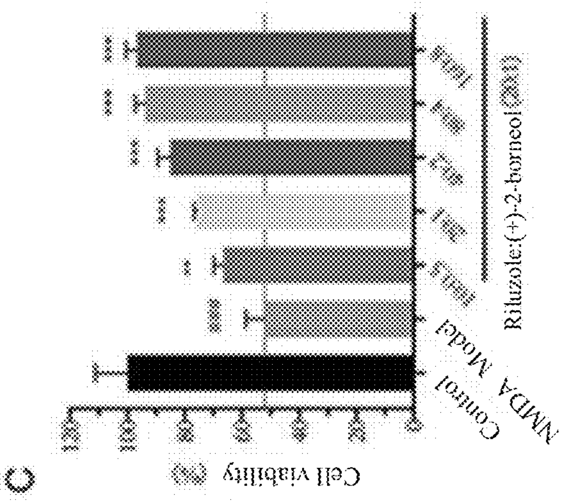
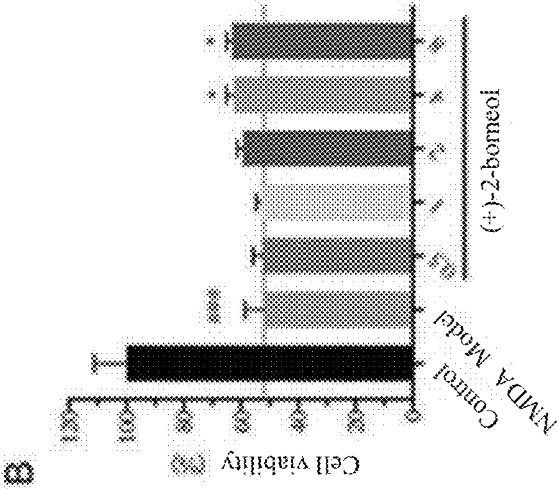
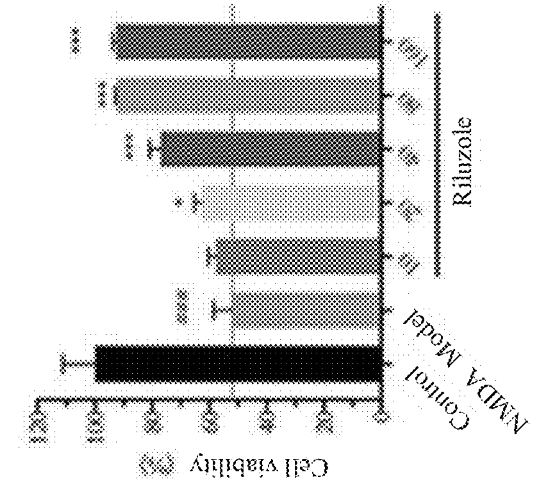
FIG. 4A-C

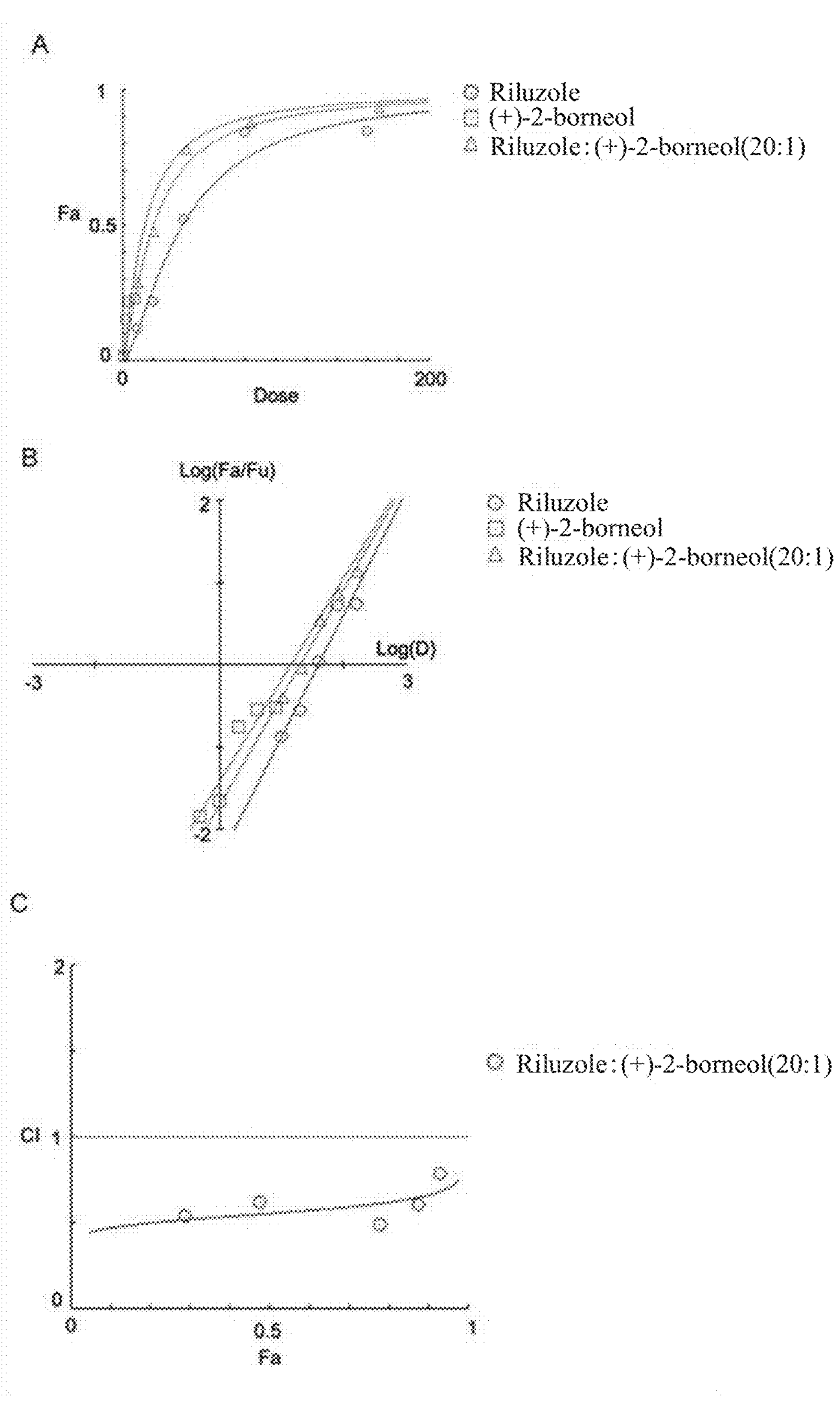
FIG. 5A-C

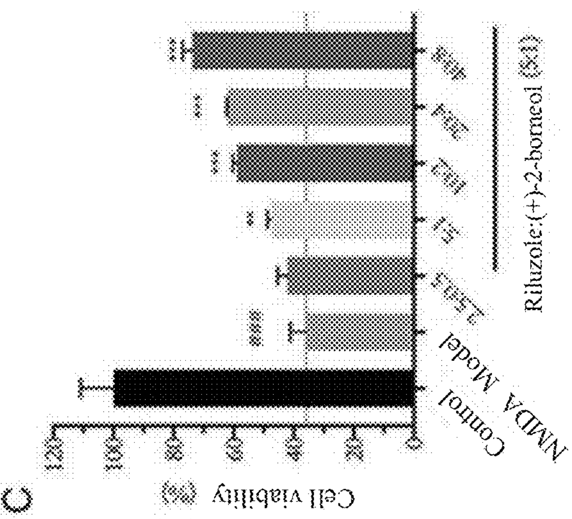
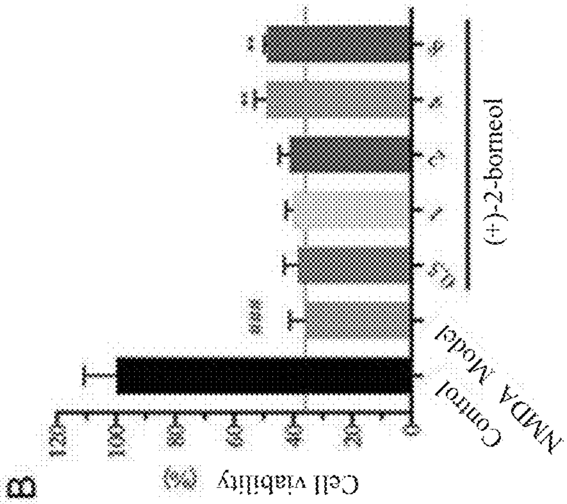
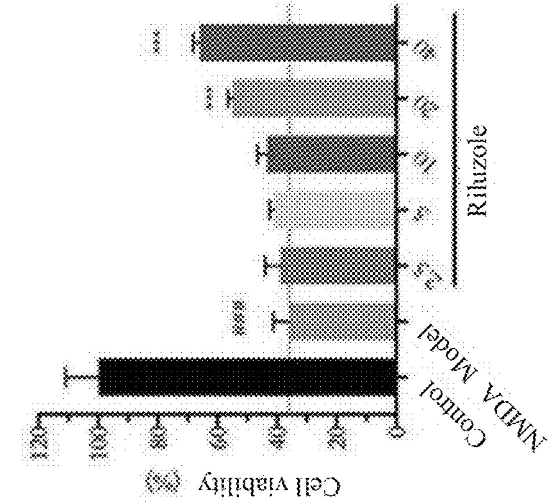
FIG. 6A-C

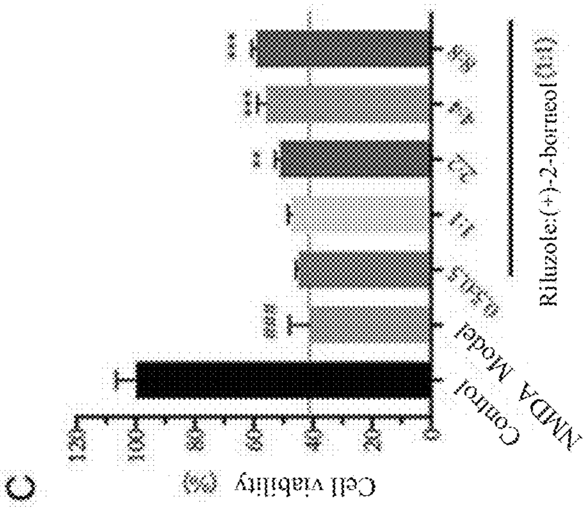
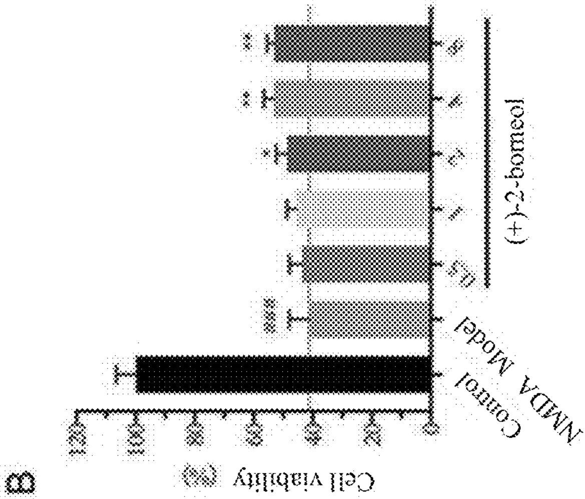
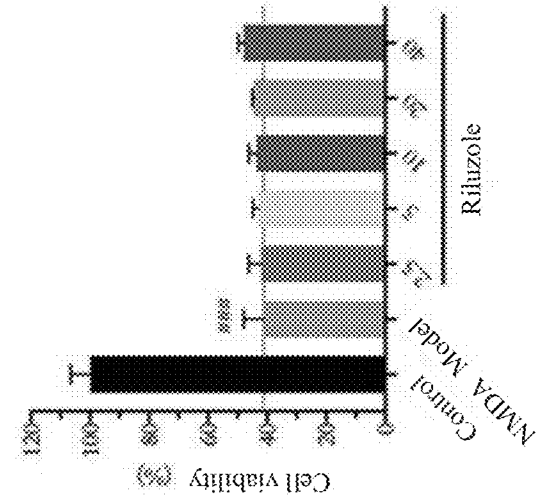
FIG. 7A-C

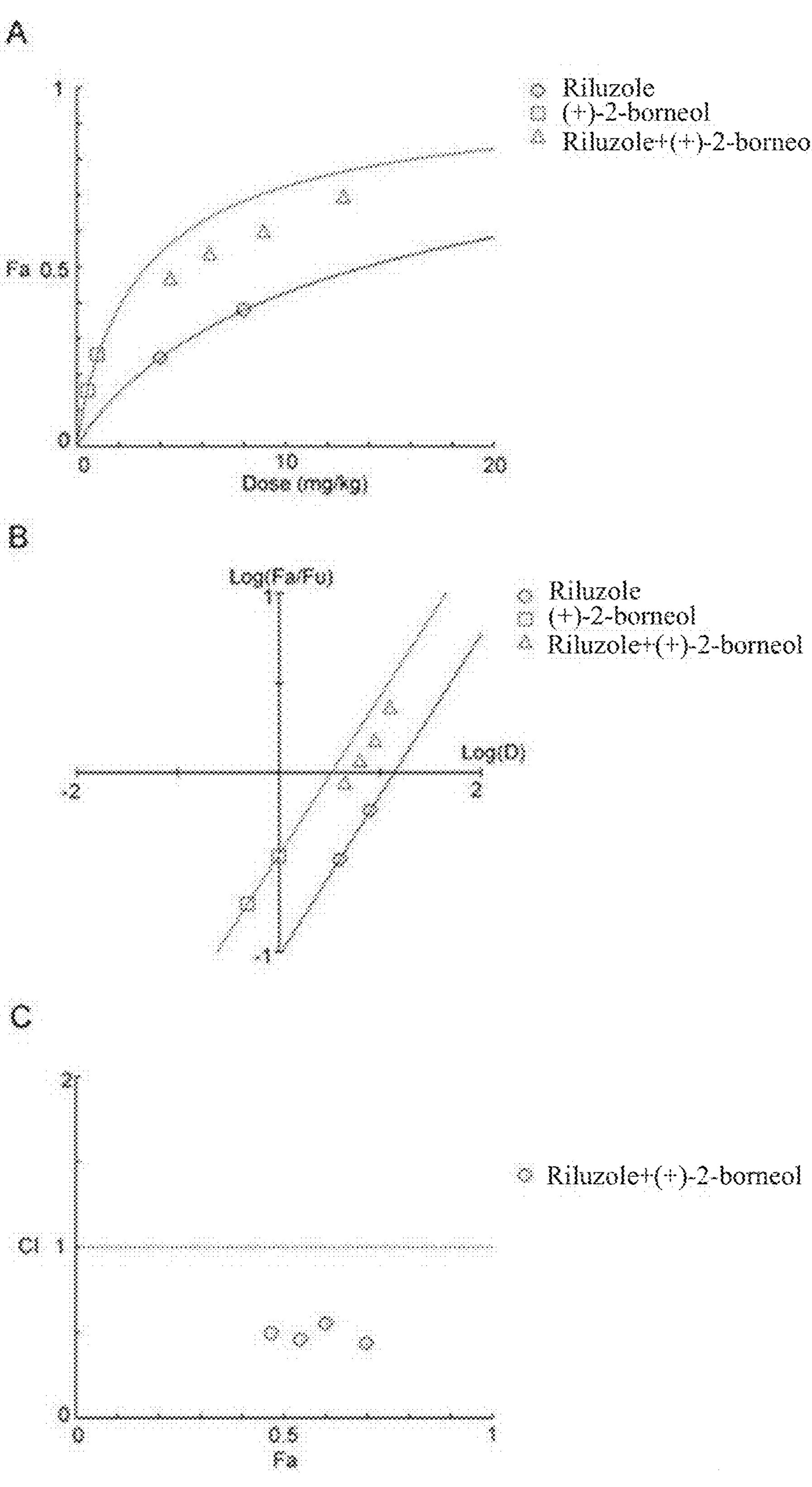
FIG. 10A-C

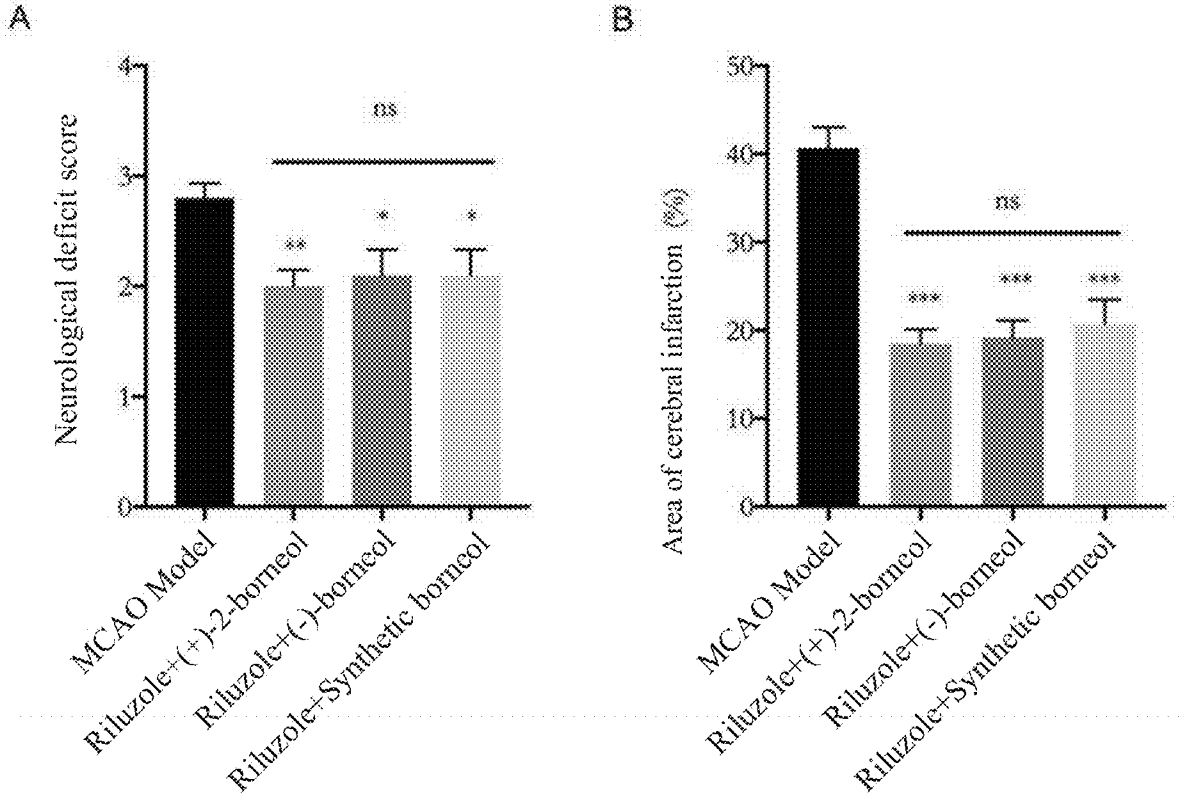
FIG. 11A-B

APPLICATION OF RILUZOLE- AND BORNEOL-CONTAINING COMPOSITION IN PREPARATION OF MEDICATION FOR TREATING CEREBROVASCULAR DISEASES

CROSS REFERENCE TO RELATED APPLICATIONS

This application is a National Phase application under 35 U.S.C. § 371 of International Application No. PCT/CN2022/073909, titled "APPLICATION OF RILUZOLE- AND BORNEOL-CONTAINING COMPOSITION IN PREPARATION OF MEDICATION FOR TREATING CEREBROVASCULAR DISEASES." filed on Jan. 26, 2022, which claims the priority to Chinese Patent Application No. 202110141522.3, titled "APPLICATION OF RILUZOLE- AND BORNEOL-CONTAINING COMPOSITION IN PREPARATION OF MEDICATION FOR TREATING CEREBROVASCULAR DISEASES." filed on Feb. 2, 2021, with the China National Intellectual Property Administration, which are incorporated herein by reference in their entireties.

FIELD

The present invention belongs to the field of pharmacy, and relates to use of a composition of 2-amino-6-trifluoromethoxybenzothiazole and borneol or (+)-2-borneol in the manufacture of a medicament for treating cerebrovascular diseases, in particular ischemic cerebrovascular diseases.

BACKGROUND

Cerebrovascular disease (CVD) refers to brain lesions caused by various cerebrovascular diseases, and can be divided into acute cerebrovascular disease (stroke) and chronic cerebrovascular disease according to its pathogenesis process. Acute cerebrovascular diseases include transient ischemic attack, cerebral thrombosis, cerebral embolism, hypertensive encephalopathy, cerebral hemorrhage, subarachnoid hemorrhage, etc.; chronic cerebrovascular diseases include cerebral arteriosclerosis, cerebrovascular dementia, cerebral arterial steal syndrome, Parkinson's disease, etc. Ischemic stroke is a general term for brain tissue necrosis caused by insufficient cerebral blood supply due to stenosis or occlusion of cerebral blood supply arteries (carotid artery and vertebral artery). Cerebral ischemia includes four types, transient ischemic attack (TIA), reversible neurological deficit (RIND), stroke in progressive (SIE) and complete stroke (CS). There is no cerebral infarction present in TIA, but there are cerebral infarction of different degrees present in RIND, SIE and CS.

2-Amino-6-trifluoromethoxybenzothiazole (riluzole) is a benzothiazole compound, which was originally researched and developed in the 1950s as a central muscle relaxant drug. In 1995, riluzole was approved by the US FDA for treating amyotrophic lateral sclerosis (ALS). Riluzole inhibits the release of glutamate from the cultured neurons, brain slices, and in vivo cerebral cortical neurons, which may be attributed in part to inactivation of voltage-dependent sodium channels in glutamatergic nerve terminals, and activation of pertussis toxin (PTX)-sensitive G protein-dependent signal transduction processes. Riluzole also blocks certain postsynaptic effects of glutamate by noncompetitively blocking N-methyl-D-aspartate (NMDA) receptors ($IC_{50}$ 18 μM) and kainic acid receptors ($IC_{50}$ 167 μM). In vivo, riluzole has neuroprotective, anticonvulsant and sedative effects. In a model of transient global cerebral ischemia in rodent, riluzole completely inhibits the ischemia-induced surge in release of glutamate. In vitro, riluzole protects the cultured neurons against hypoxic injury, injury caused by the toxic effects of glutamate uptake inhibitors, and injury caused by the toxic factors in the cerebrospinal fluid of patients with amyotrophic lateral sclerosis (Neurology, 1996, 47 (6 Suppl 4), S233S-41). Afterwards, it is found through preclinical animal and clinical human trials that riluzole has certain therapeutic effects on spinal cord neuroprotection, neuralgia, epilepsy, anxiety and depression (Chinese Pharmaceutical Journal, 2015, 50 (14): 1165-1168; Chemical and Biological Engineering, 2017, 34(2): 6-9). In addition, in a systematic review and meta-analysis of riluzole for treating neurodegenerative motor diseases, including PD, atypical Parkinson's disease, Huntington disease (HD), hereditary ataxia, etc., it is indicated that the effect of riluzole on symptoms in patients with hereditary ataxia seems promising, but further clinical validation studies are still needed (Drug Delivery, 2017, 25(1), 43-48). In addition, in the rat middle cerebral artery occlusion (MCAO) model, a single intravenous injection of riluzole given at 4 mg/kg and 8 mg/kg at 30 min after ischemia can significantly reduce the neurological deficit score and cerebral infarction area (CNS Drug Reviews, 1997, 3(1), 83-101).

Riluzole has a chemical structural formula as follows:

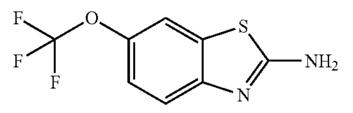

Riluzole
(molecular formula $C_8H_5F_3N_2OS$; molecular weight 234.20)

Natural borneol is the crystal extracted and processed from the fresh branches and leaves of *Cinnamomum camphora*, and has a main component of (+)-2-borneol (the 2015 edition of the Chinese Pharmacopoeia stipulates that the content of (+)-2-borneol in natural borneol should not be less than 96.0%). L-borneolum is the crystal extracted and processed from the fresh leaves of *Blumea balsamifera*, and has a main component of (−)-borneol (the 2015 edition of the Chinese Pharmacopoeia stipulates that the content of (−)-borneol in natural borneol should not be less than 85.0%). The synthetic borneol is chemically synthesized, and has main components of (+)-2-borneol and (−)-borneol. (+)-2-Borneol exhibits multiple biological activities, such as anti-inflammation, anti-oxidation, and enhancement of function of γ-aminobutyric acid (GABA) receptor (Euro J Pharmacol, 2017 811, 1-11). In addition, under physiological conditions, (+)-2-borneol can also provide delivery of central nervous system drug by temporarily reversibly increasing the permeability of the blood-brain barrier (BBB); under pathological conditions, (+)-2-borneol can maintain the integrity of the BBB and protect brain tissue (Drug Deliv 2017, 24:1037-1044; Drug Deliv 2018, 25:1617-1633; Biomed Pharmacother 2018, 102:874-883). In *Xenopus laevis* oocytes, (+)-2-borneol can enhance the function of recombinant human $GABA_AR$ ($\alpha_1\beta_2\gamma_{2L}$) induced by low concentration of GABA by more than 10 times, which has an $EC_{50}$ of 248 μM (Biochemical Pharmacology, 2005, 69(7), 1101-1111). Natural borneol has a protective effect on glutamate-induced neuronal injury (Journal of Nanjing Medical University (Natural Science Edition) 2013, 33 (5), 630-635). In addition, (+)-2-borneol has been used as a raw material drug in the Class 1 new drug Edaravone (+)-2-borneol injection for treating ischemic stroke (CDE acceptance number CXHS1800031).

(+)-2-Borneol has a chemical structural formula as follows:

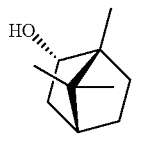

(+)-2-Borneol
(molecular formula $C_{10}H_{18}O$;
molecular weight 154.25)

Therefore, it is of important practical significance to provide use of a composition comprising riluzole and borneol in cerebrovascular diseases.

SUMMARY

In view of this, the present invention provides use of a composition comprising riluzole and borneol in the manufacture of a medicament for treating a cerebrovascular disease. The composition comprises 2-amino-6-trifluoromethoxybenzothiazole or a pharmaceutically acceptable salt thereof and borneol or (+)-2-borneol. Further, the composition comprises 2-amino-6-trifluoromethoxybenzothiazole or a pharmaceutically acceptable salt thereof and (+)-2-borneol.

In order to achieve the above purpose of the present invention, the present invention provides the following technical solutions:

in the first aspect, the present invention provides a composition comprising the following components:

- component (I), 2-amino-6-trifluoromethoxybenzothiazole, a derivative, a pharmaceutically acceptable salt or a prodrug molecule thereof; and
- component (II), (+)-2-borneol, borneol, or a drug with an active ingredient of (+)-2-borneol.

In some specific embodiments of the present invention, the component (I) and the component (II) are in a weight ratio of 30:1-1.5:1 or 27:1-1:27.

In some specific embodiments of the present invention, the component (I) and the component (TI) are in a weight ratio of 15:1-1.5:1.

In some specific embodiments of the present invention, the component (I) and the component (II) are in a weight ratio of 15:1-7.5:1.

In some specific embodiments of the present invention, the component (I) and the component (II) are in a weight ratio of 1:1, 1:3, 3:1, 9:1, 27:1, 1:9, 1:27, 20:1, 5:1, 15:1 and/or 8:1.

In some specific embodiments of the present invention, the borneol is selected from the group consisting of synthetic borneol, (−)-borneol, natural borneol and a combination thereof.

In the second aspect, the present invention further provides a drug comprising the composition and a pharmaceutically acceptable adjuvant.

In the third aspect, the present invention further provides use of the composition or the drug in the manufacture of a medicament for preventing and/or treating cerebrovascular diseases.

In some specific embodiments of the present invention, the cerebrovascular disease is selected from ischemic cerebrovascular disease.

In some specific embodiments of the present invention, the ischemic cerebrovascular disease is selected from ischemic stroke.

The borneol described in the above composition is selected from the group consisting of natural borneol, (−)-borneol and synthetic borneol.

The drug composition of the present invention can be used in the manufacture of a medicament for treating a cerebrovascular disease. Among them, the cerebrovascular disease is preferably ischemic cerebrovascular disease, more preferably ischemic stroke.

The present invention has the following beneficial effects:

The present invention combines 2-amino-6-trifluoromethoxybenzothiazole and (+)-2-borneol. The results of non-clinical cell tests and animal efficacy tests show that 2-amino-6-trifluoromethoxybenzothiazole and (+)-2-borneol have a synergistic effect on cerebrovascular disease.

BRIEF DESCRIPTION OF DRAWINGS

FIG. 1 shows the effects of riluzole and (+)-2-borneol on NMDA-induced neuronal injury; wherein, A shows the effect of riluzole on NMDA-induced neuron injury; B shows the effect of (+)-2-borneol on NMDA-induced neuron injury;

FIG. 2 shows the inhibitory rate of NMDA-induced neuronal injury by riluzole and (+)-2-borneol;

FIG. 4 shows the effect of riluzole, (+)-2-borneol and the composition (20:1) on NMDA-induced nerve excitability injury; wherein A shows the effect of riluzole, (+)-2-borneol and the composition (20:1) on NMDA-induced nerve excitability injury; B shows the effect of (+)-2-borneol on NMDA-induced nerve excitability injury; C shows the effect of the composition of riluzole and (+)-2-borneol (20:1) on NMDA-induced nerve excitability injury;

FIG. 5 shows the dose-effect curve (A), median-effect plot (B) and Fa-CI plot (C) of the composition of riluzole and (+)-2-borneol (20:1) calculated by CompuSyn software:

FIG. 6 shows the effects of riluzole, (+)-2-borneol and the composition (5:1) on NMDA-induced nerve excitability injury; wherein, A shows the effect of riluzole on NMDA-induced nerve excitability injury; B shows the effect of (+)-2-borneol on NMDA-induced nerve excitability injury; C shows the effect of the composition of riluzole and (+)-2-borneol (5:1) on NMDA-induced nerve excitability injury;

FIG. 7 shows the effects of riluzole, (+)-2-borneol and the combination (1:1) on NMDA-induced nerve excitability injury; wherein, A shows the effect of riluzole on NMDA-induced nerve excitability injury; B shows the effect of (+)-2-borneol on NMDA-induced nerve excitability injury; C shows the effect of the composition of riluzole and (+)-2-borneol (1:1) on NMDA-induced nerve excitability injury;

FIG. 10 shows the dose-effect curve (A), median-effect plot (B) and Fa-CI plot (C) of the compositions of riluzole and (+)-2-borneol (with a mass ratio of 8:1 and 15:1) reducing the cerebral infarction area of MCAO rats calculated by CompuSyn software;

FIG. 11 shows the effect of the compositions of riluzole with (+)-2-borneol, (−)-borneol or synthetic borneol on neurological deficit score and cerebral infarction area in MCAO rats; wherein, A shows the effect of the compositions of riluzole with (+)-2-borneol, (−)-borneol or synthetic borneol on neurological deficit score in MCAO rats; B shows the effect of the compositions of riluzole with (+)-2-borneol, (−)-borneol or synthetic borneol on the cerebral infarction area in MCAO rats.

DETAILED DESCRIPTION

Figure 3:
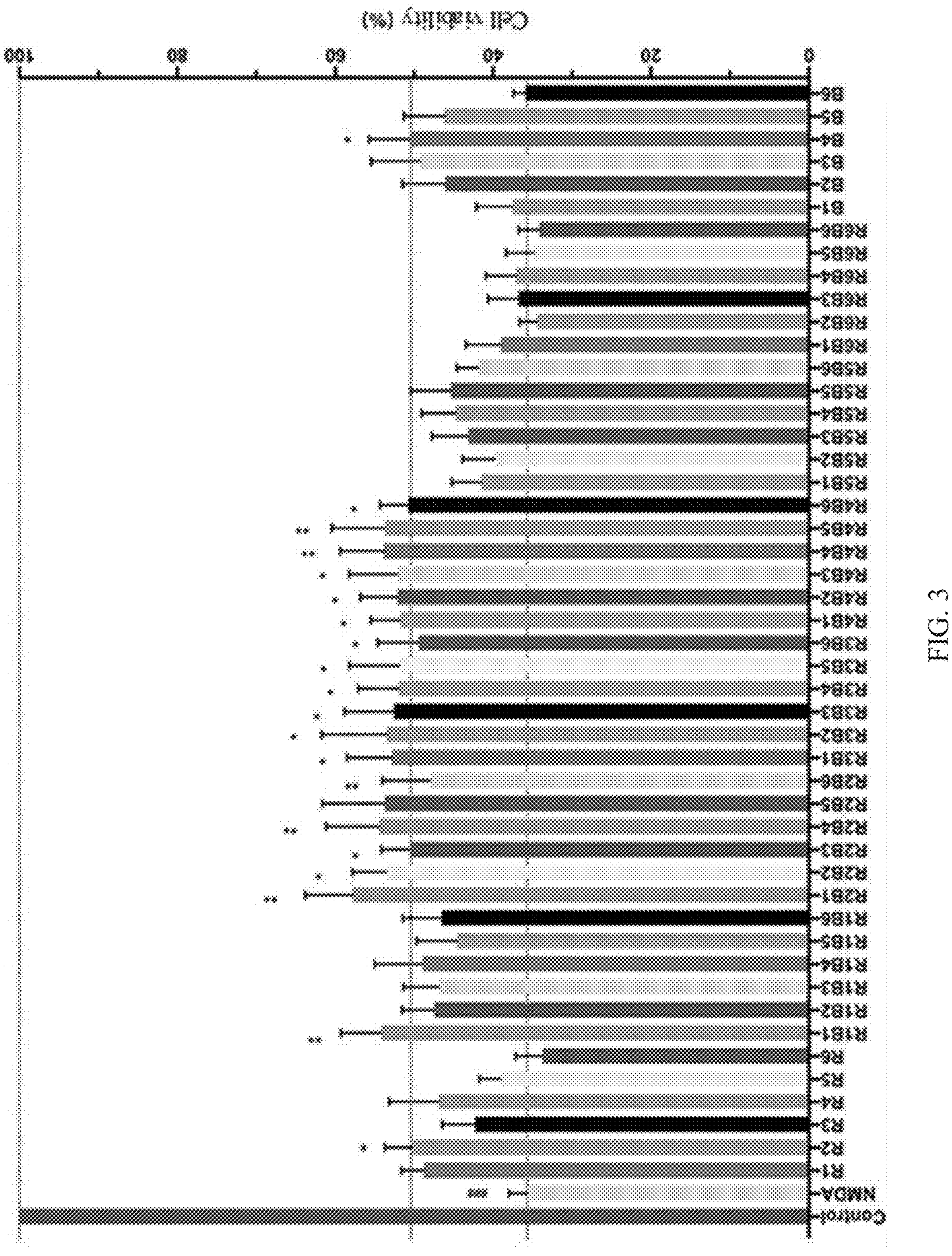
FIG. 3 shows the effect of riluzole, (+)-2-borneol and the composition of the two on the excitatory injury of NMDA-induced primary neurons.

The present invention discloses use of a composition comprising riluzole and borneol in the manufacture of a medicament for treating a cerebrovascular disease. Those skilled in the art can refer to the content of this article and appropriately improve the process parameters to realize the present invention. In particular, it should be noted that all similar replacements and modifications are apparent to those skilled in the art, and they are all considered to be included in the present invention. The method and use of the present invention have been described through preferred embodiments, and those skilled in the art can apparently make modifications or appropriate changes and combinations of the method and use described herein without departing from the content, spirit and scope of the present invention to realize and apply the technology of the present invention.

In the use of a composition comprising riluzole and borneol in the manufacture of a medicament for treating a cerebrovascular disease provided by the present invention, the raw materials and reagents used were all commercially available.

The present invention will be further illustrated below in conjunction with examples: Example 1 Effects of riluzole and (+)-2-borneol on NMDA-induced excitatory injury of primary cortical neurons

1 Materials and Methods

1.1 Animals

SD pregnant rats, Shanghai Slac Experimental Animal Co., Ltd. (production license number: SCXK (Shanghai) 2017-0005)

1.2 Reagents and Consumables

| Name | Catalogue number/ batch number | Manufacturer |
|---|---|---|
| Neurobasal | 21103-049 | Gibco |
| B27 | 17504-044 | Gibco |
| GlutaMax | 2110349 | Gibco |
| CellTiter-Glo | G7571 | Promega |
| Poly-D-lysine (PDL) | P6407 | Sigma |
| DMEM | 11995-040 | Gibco |
| Sugar-free DMEM | 1763966 | Gibco |
| Pennicillin Streptomycin (P/S) | 15140-122 | Gibco |
| Fetal Bovine Serum (FBS) | 10099-141 | Gibco |
| Cell Culture Plate | Corning 3610/96 well cell culture plate | Corning |
| Riluzole | R129533-5g (Lot1502089) | Aladdin |

-continued

| Name | Catalogue number/ batch number | Manufacturer |
|---|---|---|
| (+)-2-Borneol | KC20171205-1-2 | Jiangsu Simovay Pharmaceutical Co., Ltd. |
| CellCounting-Lite 2.0 Luminescent Cell Viability Assay | LOT 7E322D9 | Nanjing vazyme Medical Technology Co., Ltd. |

1.3 Preparation of Primary Cortical Neurons

Pregnant SD rats at 18 days of pregnancy were sacrificed by cervical dislocation. The uterus of rats was dissected and the brain of E18 fetal rats was taken out. The cerebral cortex tissue of the fetal rats was separated into ice-cold DMEM. The meninges and blood vessels on the cortical tissue were removed under a dissecting microscope. The cortical tissue was transferred into ice-cold DMEM, cut into pieces (about 1 $mm^3$), and digested with trypsin at 37° C. for 10 min. The digestion was stopped with FBS. The obtained cells were blown gently with a Pasteur pipette and passed through a 200-mesh sieve. The filtered cell suspension was transferred to a 15 mL centrifuge tube, and centrifuged at 1000 rpm for 5 min. The supernatant was discarded. Then the cell mass at the bottom of the centrifuge tube was blown gently with 37° C.-prewarmed complete medium (Neurobasal+B27+GlutaMax+1% P/S). The cells were counted using a hemocytometer, diluted to $5\times10^5$ cells/mL with complete medium, and seeded in a 96-well plate coated with PDL (100 μL/well). Half of the cell culture medium was replaced with complete medium the next day. The cells were cultured in vitro until the 11th day when the neurons differentiated and matured, and then used for the oxygen-glucose deprivation test.

1.4 NMDA-Induced Excitatory Injury Test on Primary Cortical Neurons

The culture medium of the primary neurons matured in vitro was replaced with different concentrations (100, 33.3, 11.1, 3.7, 1.23 and 0.41 μM) of riluzole (R) or (+)-2-borneol in Locke's buffer (NaCl 154 mM, KCl 5.6 mM, $NaHCO_3$ 3.6 mM, $CaCl_2$ 2.3 mM, D-Glucose 5.6 mM, HEPES 5 mM, pH7.4). After incubation at 37° C. for 10 min, an excitatory inducing agent (NMDA at a final concentration of 100 μM and glycine at a final concentration of 10 μM) was added to induce cells for 30 min. After the inducing buffer was discarded, the cells were washed once with a Locke's buffer containing 1 mM $MgCl_2$, and recovered to be incubated for 4 h by replacing with a complete medium (100 μL/well).

1.5 Determination of Viability of Neuron Cells

The viability of the primary neuron cells was determined by Luminescent Cell Viability Assay kit. According to the instruction, reagents were added at 100 μL/well, and shaking was performed for 10 min. The chemiluminescence value (LUM) was read on the SpectraMax i3X (Molecule Device) multifunctional plate reader, and the relative activity of neurons was calculated.

Calculation formula: relative neuron activity V (%)=$(LUM-LUM_{background})/(LUM_{normal\ control\ group}-LUM_{background\ group})\times100\%$. $LUM_{background}$ was the background reading of the Luminescent Cell Viability Assay reagent added to the cell-free complete medium well.

1.6 Neuroprotective Effects of Compounds

The neuroprotective effect of the compounds on excitatory injury was indicated by using the compounds to inhibit excitatory injury of neurons. Relative inhibition rate=100%×($V_{compound}$−$V_{NMDA\ model}$)/($V_{normal\ control\ group}$−$V_{NMDA\ model}$), where V represents the relative activity of neurons.

Fitting of $EC_{50}$ of compounds: Log[compound concentration] was used as the abscissa and the relative inhibition rate was used as the ordinate. Log(inhibitor) vs. response—variable slope (four parameters) curve was fitted by Prism8 (GraphPad) to obtain the $IC_{50}$ of the compounds.

1.7 Statistics

The experimental data are expressed as mean±standard deviation (Mean±SD) (n=3). After performing one-way analysis of variance (ANOVA) with Prism 8 (GraphPad), the differences between two groups were analyzed with Uncorrected Fisher's LSD. P<0.05 means significant difference. ###p<0.001, compared with the control group; *p<0.05, p<0.01, *p<0.001, compared with the NMDA model group.

2 Experimental Results 2.1 Effects of Riluzole and (+)-2-Borneol on NMDA-Induced Neuron Injury Within the concentration range of 0.41-100 μM, riluzole concentration-dependently increased the viability of neurons induced by NMDA, and it could significantly increase the viability of neurons at the concentrations of 33.3 and 100 μM (FIG. 1A). Within the concentration range of 0.41-3.7 μM, (+)-2-borneol concentration-dependently increased the viability of neurons with excitatory injury, but as the concentration increased (10-100 μM), the viability of neurons tended to decrease (FIG. 1B).

According to the compound concentration-inhibition rate curve, the $EC_{50}$ of riluzole and (+)-2-borneol for neuroprotection was about 40 μM ($E_{max}$~60%) and 2 μM ($E_{max}$~15%), respectively (FIG. 2).

Example 2 Effects of Compositions of Riluzole and (+)-2-Borneol on NMDA-Induced Excitatory Injury of Primary Cortical Neurons 1 Materials and Methods 1.1 Animals were the Same as in Example 1.

1.2 Reagents and Consumables were the Same as in Example 1.

1.3 Preparation of Primary Cortical Neurons was Conducted by the Same Method as in Example 1.

1.4 Experiment of NMDA-Induced Excitatory Injury of Primary Cortical Neurons

The culture medium of the primary neurons matured in vitro was replaced with different concentrations of riluzole (R), (+)-2-borneol (B) or compositions of riluzole and (+)-2-borneol (RB) in Locke's buffer (NaCl 154 mM, KCl 5.6 mM, $NaHCO_3$ 3.6 mM, $CaCl_2$ 2.3 mM, D-Glucose 5.6 mM, HEPES 5 mM, pH7.4)(See Table 1). After incubation at 37° C. for 10 min, an excitatory inducing agent (NMDA at a final concentration of 100 μM and glycine at a final concentration of 10 μM) was added to induce cells for 30 min. After the inducing buffer was discarded, the cells were washed once with a Locke's buffer containing 1 mM $MgCl_2$, and recovered to be incubated for 4 h by replacing with a complete medium (100 μL/well).

TABLE 1

Orthogonal design of compositions of riluzole and (+)-2-borneol

| DMSO | R1 | R2 | R3 | R4 | R5 | R6 |
|---|---|---|---|---|---|---|
| B1 | R1 B1 | R2B1 | R3B1 | R4B1 | R5B1 | R6B1 |
| B2 | R1 B2 | R2B2 | R3B2 | R4B2 | R5B2 | R6B2 |
| B3 | R1 B3 | R2B3 | R3B3 | R4B3 | R5B3 | R6B3 |
| B4 | R1 B4 | R2B4 | R3B4 | R4B4 | R5B4 | R6B4 |
| B5 | R1 B5 | R2B5 | R3B5 | R4B5 | R5B5 | R6B5 |
| B6 | R1B6 | R2B6 | R3B6 | R4B6 | R5B6 | R6B6 |

Note:
R represents riluzole, B represents (+)-2-borneol, $R_XB_Y$ represents compositions of riluzole and (+)-2-borneol, X/Y of 1-6 represents the concentrations of the respective compounds, respectively 100, 33.3, 11.1, 3.7, 1.23 and 0.41 μM. Each group of drugs had 5 replicate wells (n = 5). All compounds were first dissolved in DMSO, and the final concentration of DMSO in the cell culture medium was 0.2%.

1.5 Determination of Viability of Neuron Cells was Performed by the Same Method as in Example 1.

1.6 Statistics was Performed by the Same Method as in Example 1.

The experimental data are expressed as mean±standard deviation (Mean±SD) (n=3). After performing one-way ANOVA with Prism 8 (GraphPad), the differences between two groups were analyzed with Uncorrected Fisher's LSD. P<0.05 means significant difference. ###p<0.001, compared with Control (control group); *p<0.05, **p<0.01, compared with NMDA model group.

2 Experimental Results 2.1 Effects of Compositions of Riluzole and (+)-2-Borneol on Excitatory Injury of Primary Neurons As shown in FIG. 3, within the concentration range of 0.41-100 μM, riluzole alone at the concentration of R2 (33.3 μM) can significantly increase the viability of neurons with NMDA-induced excitatory injury. (+)-2-Borneol at the concentration of R4 (3.7 μM) can significantly improve the viability of neurons with NMDA-induced excitatory injury. The compositions of riluzole and (+)-2-borneol, namely R1B1 (1:1), R2B1 (1:3), R2B2 (1:1), R2B3 (3:1), R2B4 (9:1), R2B5 (27:1), R3B1 (1:9), R3B2 (1:3), R3B3 (1:1), R3B4 (3:1), R3B5 (9:1), R3B6 (1:27), R4B1 (1:27), R4B2 (1:9), R4B3 (1:3), R4B4 (1:1), R4B5 (3:1) and R4B6 (9:1) can significantly improve the viability of neurons induced by NMDA. This indicates that the combination of riluzole and (+)-2-borneol at a ratio of 27:1 to 1:27 may produce a synergistic effect on neuroprotection.

Example 3 Study of Synergistic Effect of Compositions of Riluzole and (+)-2-Borneol (20:1) on Protecting Primary Neurons from Excitatory Injury 1 Materials and Methods 1.1 Animals were the same as in Example 1.

1.2 Reagents and Consumables were the Same as in Example 1.

1.3 Preparation of Primary Cortical Neurons was Performed by the Same Method as in Example 1.

1.4 Experiment of NMDA-Induced Excitatory Injury of Primary Cortical Neurons

The culture medium of the primary neurons matured in vitro was replaced with different concentrations of riluzole (R), (+)-2-borneol (B) or compositions of riluzole and (+)-2-borneol (20:1) in Locke's buffer (See Table 2). After incubation at 37° C. for 10 min, an excitatory inducing agent (NMDA at a final concentration of 100 μM and glycine at a final concentration of 10 μM) was added to induce cells for 30 min. After the inducing buffer was discarded, the cells were washed once with a Locke's buffer containing 1 mM $MgCl_2$, and recovered to be incubated for 4 h by replacing with a complete medium (100 μL/well).

TABLE 2

Concentration design of compositions of riluzole and (+)-2-borneol

| Composition | Riluzole (μM) | (+)-2-Borneol (μM) |
|---|---|---|
| Riluzole | 10 | / |
| | 20 | / |
| | 40 | / |
| | 80 | / |
| | 160 | / |
| (+)-2-Borneol | / | 0.5 |
| | / | 1 |
| | / | 2 |
| | / | 4 |
| | / | 8 |
| Riluzole:(+)-2-borneol = 20:1 | 10 | 0.5 |
| | 20 | 1 |
| | 40 | 2 |
| | 80 | 4 |
| | 160 | 8 |

1.5 Determination of Viability of Neuron Cells was Performed by the Same Method as in Example 1.

1.6 Neuroprotective Effects of Compounds were Determined by the Same Method as in Example 1.

1.7 Analysis of Synergistic Effect of Compositions

The synergistic effect on neuroprotection of the compositions of riluzole and (+)-2-borneol at the fixed ratio was analyzed using CompuSyn software (ComboSyn, Inc).

1.8 Statistics

The experimental data are expressed as mean±standard deviation (Mean±SD) (n=3-6). After performing one-way ANOVA with Prism 8 (GraphPad), the differences between two groups were analyzed with Uncorrected Fisher's LSD. $P<0.05$ means significant difference. ###$p<0.001$ compared with control group; *$p<0.05$, $p<0.01$, *$p<0.001$, compared with NMDA model group.

2 Experimental Results 2.1 Effects of Riluzole, (+)-2-Borneol and Compositions of the Two (20:1) on Excitatory Injury of Primary Neurons According to the results of Example 1, the concentrations of the compounds were designed to be ¼×ED50, ½×ED50, 1×ED50, 2×ED50 and 4×ED50, where the concentrations of riluzole were 10, 20, 40, 80 and 160 μM, the concentrations of (+)-2-borneol were 0.5, 1, 2, 4 and 8 μM, and the molar ratio of the compositions of riluzole and (+)-2-borneol was 20:1. Riluzole, (+)-2-borneol and the compositions of the two can concentration-dependently increase the viability of neurons with injury induced by NMDA, and the effect of the compositions was better than that of riluzole or (+)-2-borneol (FIG. 3).

2.2 Analysis of Synergistic Effect on Neuroprotection of Compositions of Riluzole and (+)-2-Borneol According to the principle of the Chou-Talalay equation, the combination index (CI) of the compositions at the fixed ratio was calculated using CompuSyn software (see Table 3, FIG. 5), and the compositions of riluzole and (+)-2-borneol at the molar ratio of 20:1 had CI<1, indicating that riluzole and (+)-2-borneol have a synergistic effect on protecting neurons from excitatory injury.

TABLE 3

Effect (Fa) and combination index (CI) of compositions of riluzole and (+)-2-borneol in protecting neurons from excitatory injury

| Riluzole | | (+)-2-Borneol | | Composition of riluzole/ (+)-2-borneol (20:1) | | |
|---|---|---|---|---|---|---|
| Concentration (μM) | Fa | Concentration (μM) | Fa | Concentration (μM) | Fa | CI |
| 160 | 0.847 | 8 | 0.231 | 160/8 | 0.932 | 0.784 |
| 80 | 0.842 | 4 | 0.22 | 80/4 | 0.878 | 0.608 |
| 40 | 0.523 | 2 | 0.152 | 40/2 | 0.78 | 0.492 |
| 20 | 0.219 | 1 | 0.022 | 20/1 | 0.477 | 0.621 |
| 10 | 0.118 | 0.5 | 0.014 | 10/0.5 | 0.288 | 0.542 |

Example 4 Study of Synergistic Effect of Compositions of Riluzole and (+)-2-Borneol (5:1) on Protecting Primary Neurons from Excitatory Injury

1 Materials and Methods 1.1 Animals were the Same as in Example 1.

1.2 Reagents and Consumables were the Same as in Example 1.

1.3 Preparation of Primary Cortical Neurons was Performed by the Same Method as in Example 1.

1.4 Experiment of NMDA-Induced Excitatory Injury of Primary Cortical Neurons

The culture medium of the primary neurons matured in vitro was replaced with different concentrations of riluzole (R), (+)-2-borneol (B) or compositions of riluzole and (+)-2-borneol (5:1) in Locke's buffer (See Table 2). After incubation at 37° C. for 10 min, an excitatory inducing agent (NMDA at a final concentration of 100 μM and glycine at a final concentration of 10 μM) was added to induce cells for 30 min. After the inducing buffer was discarded, the cells were washed once with a Locke's buffer containing 1 mM $MgCl_2$, and recovered to be incubated for 4 h by replacing with a complete medium (100 μL/well).

TABLE 4

Concentration design of compositions of riluzole and (+)-2-borneol

| Composition | Riluzole (μM) | Borneol (μM) |
|---|---|---|
| Riluzole | 2.5 | / |
| | 5 | / |
| | 10 | / |
| | 20 | / |
| | 40 | / |
| (+)-2-borneol | / | 0.5 |
| | / | 1 |
| | / | 2 |
| | / | 4 |
| | / | 8 |
| Riluzole:(+)-2-borneol = 5:1 | 2.5 | 0.5 |
| | 5 | 1 |
| | 10 | 2 |
| | 20 | 4 |
| | 40 | 8 |

1.5 Determination of Viability of Neuron Cells was Performed by the Same Method as in Example 1.

1.6 Neuroprotective Effects of Compounds were Determined by the Same Method as in Example 1.

1.7 Analysis of Synergistic Effect of Compositions

The synergistic effect on neuroprotection of the compositions of riluzole and (+)-2-borneol at the fixed ratio was analyzed using CompuSyn software (ComboSyn, Inc).

1.8 Statistics was Performed by the Same Method as in Example 3.

2 Experimental Results 2.1 Effects of Riluzole, (+)-2-Borneol and Compositions of the Two (5:1) on Excitatory Injury of Primary Neurons The concentrations of riluzole were 2.5, 5, 10, 20 and 40 μM, the concentrations of (+)-2-borneol were 0.5, 1, 2, 4 and 8 μM, and the molar ratio of the compositions of riluzole and (+)-2-borneol was 5:1. Riluzole, (+)-2-borneol and the compositions of the two can concentration-dependently increase the viability of neurons with injury induced by NMDA, and the compositions (5:1) had a better effect than riluzole or (+)-2-borneol (FIG. 6).

2.2 Analysis of Synergistic Effect on Neuroprotection of Compositions of Riluzole and (+)-2-Borneol According to the principle of the Chou-Talalay equation, the combination index (CI) of the compositions at the fixed ratio was calculated using CompuSyn software (see Table 5), and the compositions of riluzole and (+)-2-borneol at the molar ratio of 5:1 had CI<1, indicating that riluzole and (+)-2-borneol have a synergistic effect on protecting neurons from excitatory injury.

TABLE 5

Effect (Fa) and combination index (CI) of compositions of riluzole and (+)-2-borneol in protecting neurons from excitatory injury

| Riluzole | | (+)-2-Borneol | | Composition of riluzole/ (+)-2-borneol (5:1) | | |
|---|---|---|---|---|---|---|
| Concentration (μM) | Fa | Concentration (μM) | Fa | Concentration (μM) | Fa | CI |
| 40 | 0.469 | 8 | 0.205 | 40/8 | 0.592 | 0.673 |
| 20 | 0.297 | 4 | 0.209 | 20/4 | 0.408 | 0.729 |
| 10 | 0.118 | 2 | 0.086 | 10/2 | 0.358 | 0.456 |
| 5 | 0.081 | 1 | 0.069 | 5/1 | 0.182 | 0.617 |
| 2.5 | 0.048 | 0.5 | 0.042 | 2.5/0.5 | 0.100 | 0.673 |

Example 5 Study of Synergistic Effect of Compositions of Riluzole and (+)-2-Borneol (1:1) on Protecting Primary Neurons from Excitatory Injury

1 Materials and Methods 1.1 Animals were the Same as in Example 1.

1.2 Reagents and Consumables were the Same as in Example 1.

1.3 Preparation of Primary Cortical Neurons was Performed by the Same Method as in Example 1.

1.4 Experiment of NMDA-Induced Excitatory Injury of Primary Cortical Neurons

The culture medium of the primary neurons matured in vitro was replaced with different concentrations of riluzole (R), (+)-2-borneol (B) or compositions of riluzole and (+)-2-borneol (1:1) in Locke's buffer (See Table 2). After incubation at 37° C. for 10 min, an excitatory inducing agent (NMDA at a final concentration of 100 μM and glycine at a final concentration of 10 PM) was added to induce cells for 30 min. After the inducing buffer was discarded, the cells were washed once with a Locke's buffer containing 1 mM $MgCl_2$, and recovered to be incubated for 4 h by replacing with a complete medium (100 μL/well).

TABLE 6

Concentration design of compositions of riluzole and (+)-2-borneol

| Composition | Riluzole (μM) | (+)-2-Borneol (μM) |
|---|---|---|
| Riluzole | 0.5 | / |
| | 1 | / |
| | 2 | / |
| | 4 | / |
| | 8 | / |
| (+)-2-Borneol | / | 0.5 |
| | / | 1 |
| | / | 2 |
| | / | 4 |
| | / | 8 |
| Riluzole:(+)-2-borneol = 1:1 | 0.5 | 0.5 |
| | 1 | 1 |
| | 2 | 2 |
| | 4 | 4 |
| | 8 | 8 |

1.5 Determination of Viability of Neuron Cells was Performed by the Same Method as in Example 1.

1.6 Neuroprotective Effects of Compounds were Determined by the Same Method as in Example 1.

1.7 Analysis of Synergistic Effect of Compositions

The synergistic effect on neuroprotection of the compositions of riluzole and (+)-2-borneol at the fixed ratio was analyzed using CompuSyn Software (ComboSyn, Inc).

1.8 Statistics was Performed by the Same Method as in Example 3.

2 Experimental Results 2.1 Effects of Riluzole, (+)-2-Borneol and Compositions of the Two (1:1) on Excitatory Injury of Primary Neurons The concentrations of riluzole were 0.5, 1, 2, 4 and 8 μM, the concentrations of (+)-2-borneol were 0.5, 1, 2, 4 and 8 μM, and the molar ratio of the compositions of riluzole and (+)-2-borneol was 1:1. The protective effect of riluzole in this concentration range has a certain concentration-dependence. (+)-2-Borneol and the compositions (1:1) can concentration-dependently increase the viability of neurons with injury induced by NMDA. The compositions (1:1) had a better effect than riluzole or (+)-2-borneol (FIG. 7).

2.2 Analysis of Synergistic Effect on Neuroprotection of Compositions of Riluzole and (+)-2-Borneol According to the principle of the Chou-Talalay equation, the combination index (CI) of the compositions at the fixed ratio was calculated using CompuSyn software (see Table 7), and the compositions of riluzole and (+)-2-borneol at the molar ratio of 1:1 had CI<1, indicating that riluzole and (+)-2-borneol have a synergistic effect on protecting neurons from excitatory injury.

TABLE 7

Effect (Fa) and combination index (CI) of compositions of riluzole and (+)-2-borneol in protecting neurons from excitatory injury

| Riluzole | | (+)-2-Borneol | | Composition of riluzole/ (+)-2-borneol (1:1) | | |
|---|---|---|---|---|---|---|
| Concentration (μM) | Fa | Concentration (μM) | Fa | Concentration (μM) | Fa | CI |
| 8 | 0.116 | 8 | 0.202 | 8/8 | 0.202 | 0.765 |
| 4 | 0.055 | 4 | 0.205 | 4/4 | 0.205 | 0.580 |
| 2 | 0.042 | 2 | 0.128 | 2/2 | 0.128 | 0.610 |
| 1 | 0.029 | 1 | 0.077 | 1/1 | 0.077 | 0.704 |
| 0.5 | 0.017 | 0.5 | 0.042 | 0.5/0.5 | 0.042 | 0.765 |

Example 6 Study on the Protective Effect of Compositions of Riluzole and (+)-2-Borneol on Focal Cerebral Ischemia-Reperfusion Injury

1 Materials and Methods 1.1 Experimental Animals

Sprague-Dawley (SD) rats, male, SPF-grade, weighing 250-280 g.

1.2 Test Drugs

Riluzole and (+)-2-borneol were the same as in Example 1.

1.3 Experimental Method 1.3.1 Establishment of Focal Cerebral Ischemia-Reperfusion Model The rat focal cerebral ischemia-reperfusion model was established by internal carotid artery suture method. The limbs (hind limbs above the knee joint and forelimbs above the wrist joint) and head of an anesthetized rat were tightened with rubber bands. The animal was fixed on an operating table in supine position, and was shaved with an animal shaver from the head to the chest, and the skin was disinfected with alcohol. The neck of the rat was cut at the midline, and the subcutaneous tissue was bluntly separated. The thin layer of fascia on the surface of the anterior triangle of the neck was separated, the lower side-lower edge of the clavicular hyoid muscle was pulled up, and the longitudinally pulsating artery parallel to this muscle can be seen. The arterial shell was opened, and the bifurcation of the right carotid artery was exposed. The right common carotid artery, external carotid artery and internal carotid artery were separated. The vagus nerve was gently stripped, and the external carotid artery was ligated and cut. The proximal end of the common carotid artery was clamped. An incision was made at the distal end from the ligature of the external carotid artery, and was inserted with a suture line, which was passed through the bifurcation of the common carotid artery into the internal carotid artery, and then was inserted slowly until reaching slight resistance (approximately 20 mm from the bifurcation), so as to block all blood supply to the middle cerebral artery. The suture line was slightly fixed below the incision of the external carotid artery with silk thread. The silk thread clamping the proximal end of the common carotid artery was loosened. A gauze soaked in sterile saline was covered on the wound, and the rat was placed on a heat preservation pad to keep warm. 2.0 h after cerebral ischemia on the right side, the suture line was pulled out gently to restore the blood supply for reperfusion. The external carotid artery was ligated with silk thread fixing the suture line. The skin was stitched, and disinfected. The rats were placed in clean feed, and their general condition and respiration were observed until they woke up from anesthesia. The rats were provided with food and water, and commonly reared.

1.3.2 Grouping and Administration of Animals

The experimental animals were divided into riluzole groups (6 mg/kg and 12 mg/kg, i.v.), (+)-2-borneol groups (0.4 mg/kg and 0.8 mg/kg, i.v.), the composition of riluzole and (+)-2-borneol group (6.4 mg/kg and 12.8 mg/kg, i.v., riluzole: (+)-2-borneol=15:1) and model group, a total of 9 groups. After the cerebral ischemia model was established, the animals were assigned to each group in a single-blind manner with equal probability. After reperfusion, the animals were immediately administered intravenously with the drugs once. The animals in the model group were administered with an equal volume of normal saline. Neurological deficit symptoms were evaluated 24 hours after cerebral ischemia, the animals were sacrificed, and their brains were taken out, stained, and photographed for determining the area of cerebral infarction.

1.3.3 Scoring of Neurological Deficit Symptoms and Determination of Cerebral Infarction Area Neurological deficit symptoms were evaluated using the modified Bederson 5-point scale. The neurological deficit symptoms of rats after cerebral ischemia were evaluated by a single-blind method. That is, the test designer marked the animals into groups, and the tester who scored the neurological deficit symptoms did not know the grouping of the animals. After scoring, the scoring results of various markers were submitted to the designer, who unblinded and obtained the scoring of each animal in each experimental group.

TABLE 8

| Neurological deficit symptom scoring Bederson 5-point scale | |
|---|---|
| 0 | When the animal was suspended in the air by the tail, both its forelimbs were extended towards the floor, and there were no other behavioral defects. |
| 1 | When the animal was suspended in the air by the tail, its forelimb on the opposite (left) side of the surgery showed wrist and elbow flexion, shoulder internal rotation, elbow abduction and close to the chest wall. |
| 2 | When the animal was placed on a smooth flat surface, the resistance was reduced when pushing the shoulder on the surgery side to the opposite side. |
| 3 | When the animal walked freely, it circled or turned around the opposite side of the surgery. |
| 4 | The limbs were flaccid, with no spontaneous movement. |

The degree of cerebral infarction was determined by TTC staining. After the evaluation of the symptoms of neurological deficits was completed, the animals were sacrificed with $CO_2$. The brain was taken out by cutting off head. The olfactory bulb, cerebellum and lower brainstem were removed. The blood on the surface of the brain was washed with normal saline, and the residual water on the surface was removed. The brain was placed at −20° C. for 20 min, then taken out, immediately cut to a coronal section vertically downward at the crossing plane of the line of sight, and sliced backward every 2 mm. The brain slices were incubated in 1% TTC staining solution (at 37° C. for 30 min). The normal brain tissue was stained into dark red, and the ischemic brain tissue was stained into pale white. After being washed with normal saline, the brain slices were quickly arranged in a row from front to back, removed off the residual water on the surface, and photographed.

Calculation of area of cerebral infarction: The photos were processed by Image J software, and the corresponding area of left brain and non-infarction area of right brain were calculated according to the formula, so that the percentage of the area of infarction was calculated.

Calculation of Volume of Infarction:

$$V = t(A1 + A2 + A3 + \ldots + An),$$

t is the thickness of a slice, A is the area of infarction.

$$\%I = 100\% \times (V_C - V_L)/V_C,$$

% I is the percentage of volume of infarction, $V_C$ is the brain volume of the control side (left brain), and $V_L$ is the volume of the non-infarction area of the infarction side (right brain).

1.4 Analysis of Synergistic Effect of Compositions

The synergistic effect on neuroprotection of the compositions of riluzole and (+)-2-borneol at the non-fixed ratio was analyzed using CompuSyn software (ComboSyn, Inc).

1.5 Statistics

The experimental data are expressed as mean±standard deviation (Mean±SD) (n=10). After performing one-way analysis of variance (ANOVA), the differences between two groups were analyzed with Fisher's LSD. P<0.05 means significant difference. *p<0.05, p<0.01, *p<0.001, compared with the MCAO model group, ns means there is no statistical difference between the groups shown in the figure.

Figure 8:
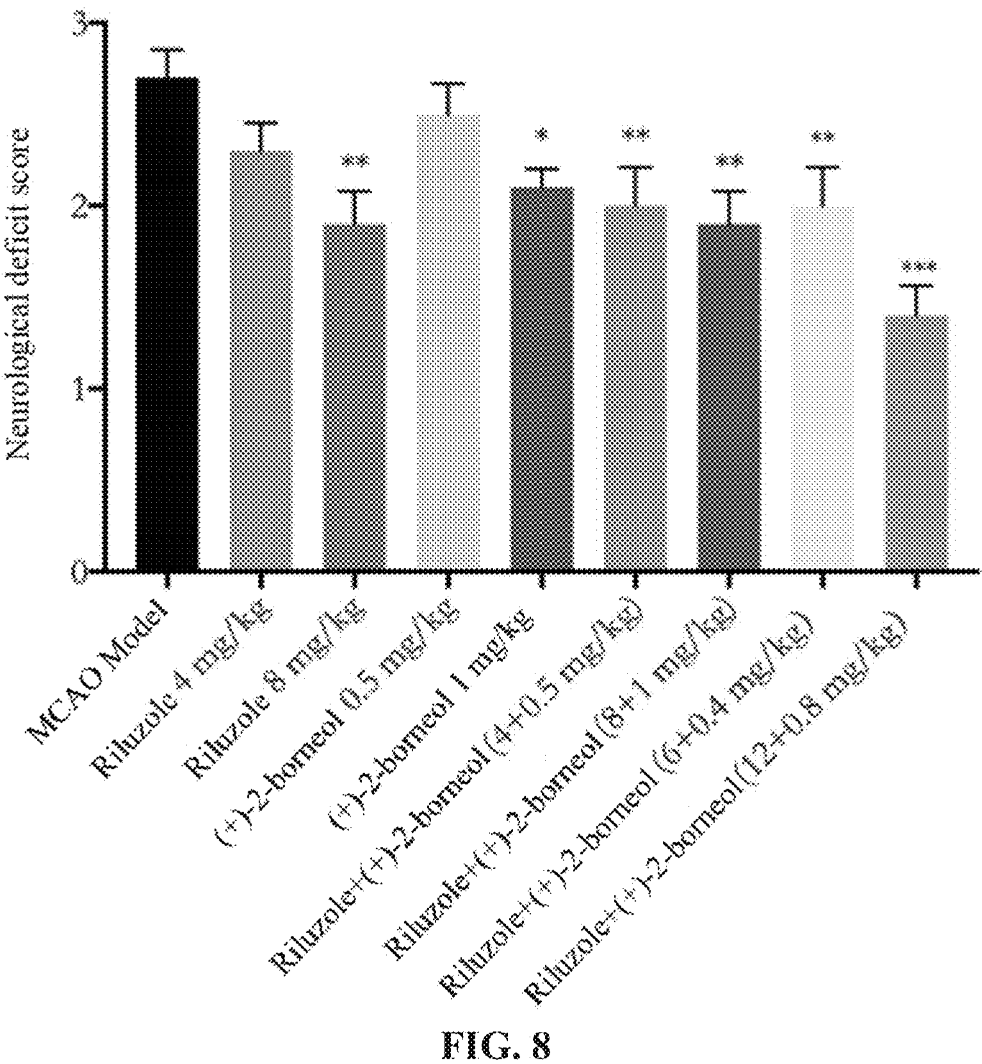
FIG. 8 shows the effect of the composition of riluzole and (+)-2-borneol on neurological deficit symptom in MCAO rats.
Figure 9:
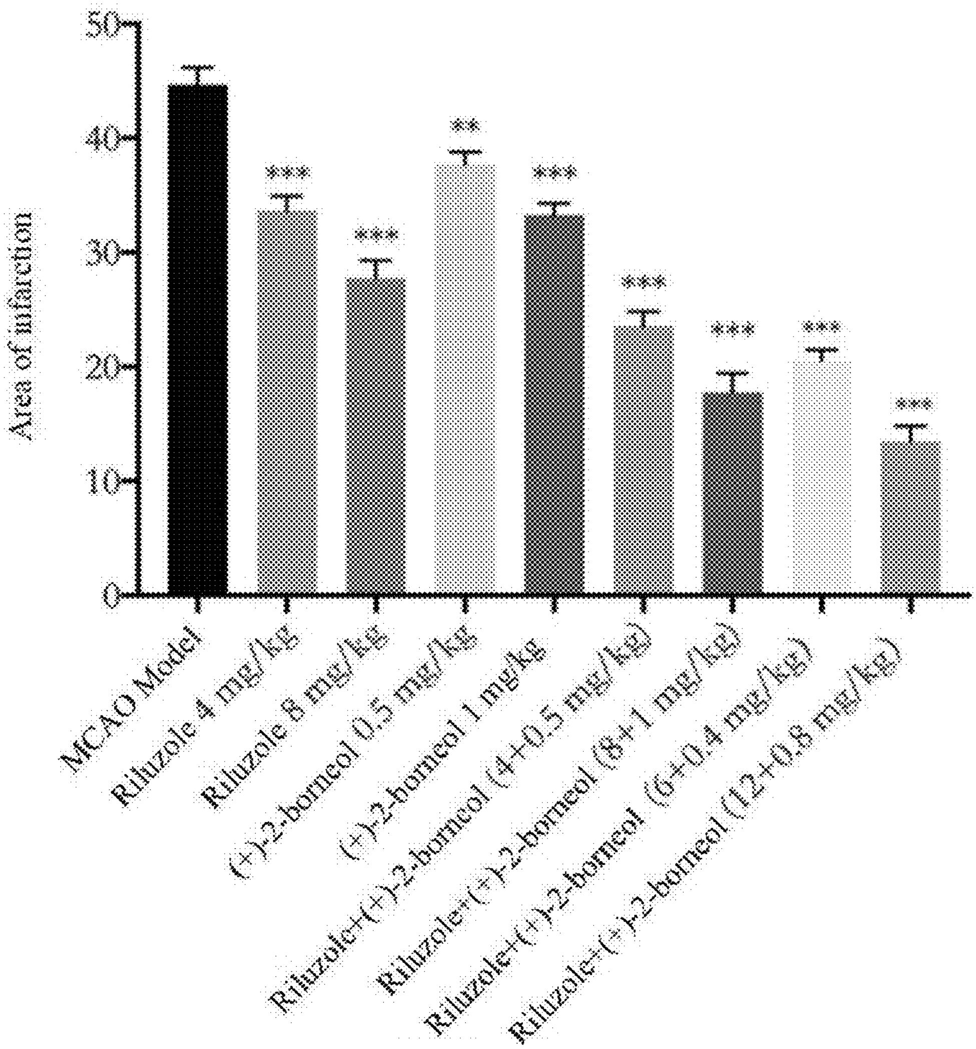
FIG. 9 shows the effect of the composition of riluzole and (+)-2-borneol on the cerebral infarction area.

2 Experimental Results 2.1 Effect of Compositions of Riluzole and (+)-2-Borneol on Neurological Deficit Symptoms As shown in FIG. 8, riluzole, (+)-2-borneol and the composition of the two can all dose-dependently reduce the neurological deficit score of MCAO rats. Compared with the MCAO model group, the neurological deficit scores of MCAO rats in the riluzole 8 mg/kg group, (+)-2-borneol 1 mg/kg group, the composition (comprising riluzole and (+)-2-borneol in a mass ratio of 8:1) 4.5 mg/kg and 9 mg/kg group, and the composition (comprising riluzole and (+)-2-borneol in a mass ratio of 15:1) 6.4 mg/kg and 12.8 mg/kg group were significantly reduced. In addition, the neurological deficit scores in the composition groups tended to be reduced lower compared to the riluzole or (+)-2-borneol groups.

2.2 Effect of Compositions of Riluzole and (+)-2-Borneol on the Area of Cerebral Infarction As shown in FIG. 8, compared with the MCAO model group, the riluzole 4 and 8 mg/kg groups, the (+)-2-borneol 0.5 and 1 mg/kg groups, the composition (comprising riluzole and (+)-2-borneol in a mass ratio of 8:1) 4.5 mg/kg and 9 mg/kg group, the composition (comprising riluzole and (+)-2-borneol in a mass ratio of 15:1) 6.4 mg/kg and 12.8 mg/kg group dose-dependently, significantly reduced cerebral infarction area. In addition, compared with the riluzole or (+)-2-borneol group, the animals in the composition groups had a lower cerebral infarction area.

2.3 Analysis of Synergistic Effect of Compositions of Riluzole and (+)-2-Borneol on Reducing Cerebral Infarction Area According to the principle of the Chou-Talalay equation, the combination index (CI) of the compositions at non-fixed ratios was calculated using CompuSyn software (see Table 9, FIG. 10), and the compositions of riluzole and (+)-2-borneol at the molar ratio of 8:1 had CI<1, indicating that riluzole and (+)-2-borneol have a synergistic effect on reducing the area of cerebral infarction in MCAO rats.

TABLE 9

Effect (Fa) and combination index (CI) of compositions of riluzole and (+)-2-borneol in reducing the area of cerebral infarction in MCAO rats

| Riluzole | | (+)-2-Borneol | | Composition of riluzole and (+)-2-borneol | | |
|---|---|---|---|---|---|---|
| Dose (mg/kg) | Fa | Dose (mg/kg) | Fa | Dose (riluzole and (+)-2-borneol) (mg/kg) | Fa | CI |
| 4 | 0.247 | 0.5 | 0.157 | 4/0.5 (8:1) | 0.472 | 0.555 |
| 8 | 0.380 | 1 | 0.256 | 8/1 (8:1) | 0.602 | 0.499 |
| / | / | / | / | 6/0.4 (15:1) | 0.541 | 0.463 |
| / | / | / | / | 12/0.8 (15:1) | 0.699 | 0.435 |

Example 7 Study on the Protective Effect of Compositions of Riluzole and (+)-2-Borneol, (−)-Borneol and Synthetic Borneol on Focal Cerebral Ischemia-Reperfusion Injury

1 Materials and Methods

1.1 Experimental Animals were the Same as in Example 6

1.2 Test Drugs

Riluzole and (+)-2-borneol were the same as in Example 1.

(−)-Borneol and synthetic borneol were purchased from Shanghai Aladdin Biochemical Technology Co., Ltd.

1.3 Experimental Method 1.3.1 Establishment of Focal Cerebral Ischemia-Reperfusion Model was the Same as in Example 6.

1.3.2 Grouping and Administration of Animals

Experimental animals were divided into the composition of riluzole and (+)-2-borneol group (8 mg/kg riluzole and 1 mg/kg (+)-2-borneol, i.v.), the composition of riluzole and (−)-borneol group (8 mg/kg riluzole and 1 mg/kg (−)-borneol), the composition of riluzole and synthetic borneol group (8 mg/kg riluzole and 1 mg/kg synthetic borneol) and model group, a total of 4 groups. After the cerebral ischemia model was established, the animals were assigned to each group in a single-blind manner with equal probability. After reperfusion, the animals were immediately administered intravenously with the drugs once. The animals in the model group were administered with an equal volume of normal saline. Neurological deficit symptoms were evaluated 24 hours after cerebral ischemia, the animals were sacrificed, and their brains were taken out, stained, and photographed for determining the area of cerebral infarction.

1.3.3 Scoring of Neurological Deficit Symptoms and Determination of Cerebral Infarction Area were the Same as in Example 6.

1.4 Statistics

The experimental data are expressed as mean±standard deviation (Mean±SD) (n=10). After performing one-way analysis of variance (ANOVA), the differences between two groups were analyzed with Fisher's LSD. $P<0.05$ means significant difference. *$p<0.05$, $p<0.01$, *$p<0.001$, compared with the MCAO model group; ns means there is no statistical difference between the groups shown in the figure.

2 Experimental Results 2.1 Effect of Compositions on Neurological Deficit Symptoms and Cerebral Infarction Area in MCAO Rats As shown in FIG. 11, the composition of riluzole (8 mg/kg) with (+)-2-borneol (1 mg/kg), (−)-borneol (1 mg/kg) or synthetic borneol (1 mg/kg) can all significantly reduce the neurological deficit score and cerebral infarction area in MCAO rats. Furthermore, in terms of neurological deficit score and cerebral infarction area, there were no differences among the three compositions.

The use of a composition comprising riluzole and borneol in the manufacture of a medicament for treating a cerebrovascular disease provided by the present invention has been introduced in detail above. Specific examples are used herein to illustrate the principle and embodiments of the present invention. The description of the above examples is only used to help understand the method and core idea of the present invention. It should be noted that for those skilled in the art, without departing from the principles of the present invention, several improvements and modifications can be made to the present invention, and these improvements and modifications also fall within the protection scope of the claims of the present invention.

The invention claimed is:

1. A composition, comprising the following components:
component (I), 2-amino-6-trifluoromethoxybenzothiazole, or a pharmaceutically acceptable salt thereof; and
component (II), (+)-2-borneol.

2. The composition according to claim 1, wherein the component (I) and the component (II) are in a weight ratio of 30:1-1.5:1.

3. The composition according to claim 1, wherein the component (I) and the component (II) are in a weight ratio of 15:1-1.5:1.

4. The composition according to claim 1, wherein the component (I) and the component (II) are in a weight ratio of 15:1-7.5:1.

5. The composition according to claim 1, wherein the component (I) and the component (II) are in a weight ratio of 1:1, 1:3, 3:1, 9:1, 27:1, 1:9, 1:27, 20:1, 5:1, 15:1 and/or 8:1.

6. A drug, comprising the composition according to claim 1 and a pharmaceutically acceptable adjuvant.

7. A method for treating ischemic stroke comprising administering the composition according to claim 1 to a subject in need thereof.

8. A method for treating ischemic stroke comprising administering the drug according to claim 6 to a subject in need thereof.

* * * * *